United States Patent [19]

Voege

[11] Patent Number: 5,219,853
[45] Date of Patent: Jun. 15, 1993

[54] AGENT FOR COCCIDIOSIS

[75] Inventor: Herbert Voege, Leverkusen, Fed. Rep. of Germany

[73] Assignee: Bayer Aktiengesellschaft, Leverkusen, Fed. Rep. of Germany

[21] Appl. No.: 572,324

[22] Filed: Aug. 22, 1990

Related U.S. Application Data

[63] Continuation of Ser. No. 108,517, Oct. 15, 1987, abandoned, which is a continuation of Ser. No. 564,455, Dec. 22, 1983, abandoned.

[30] Foreign Application Priority Data

Jan. 12, 1983 [DE] Fed. Rep. of Germany ....... 3300793

[51] Int. Cl.$^5$ ............................................. A01N 43/66
[52] U.S. Cl. .................................................. 514/241
[58] Field of Search ......................................... 514/241

[56] References Cited

U.S. PATENT DOCUMENTS 4,219,552 8/1980 Haberkorn et al. ................. 514/241

FOREIGN PATENT DOCUMENTS 0081142 6/1983 European Pat. Off.
1476867 3/1966 France.
23388559 11/1978 France.

Primary Examiner—Frederick E. Waddell
Assistant Examiner—Kevin E. Weddington
Attorney, Agent, or Firm—Sprung Horn Kramer & Woods

[57] ABSTRACT

The invention relates to water-miscible solution (and methods for the preparation) of 1-[3-methyl-4-(4'-trifluoromethylthiophenoxy)phenyl]-3-methyl-1,3,5-triazine-2,4,6(1H, 3H, 5H)trione and their use for controlling coccidiosis.

5 Claims, No Drawings

AGENT FOR COCCIDIOSIS

This application is a continuation of application Ser. No. 108,517, filed Oct. 15, 1987 which is a continuation of Ser. No. 564,455, filed Dec. 22, 1983, both now abandoned.

The invention relates to water-miscible solutions of 1-[3-methyl-4-(4'-trifluoromethylthiophenoxy)phenyl]-3-methyl-1,3,5-triazin-2,4,6(1H,3H,5H)-trione and their use for controlling coccidiosis.

The abovementioned compound, the chemical structural formula of which is shown below,

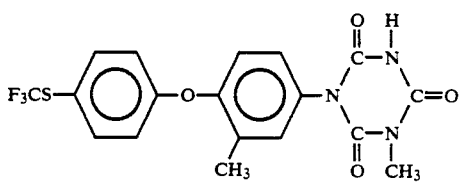

is known as an active compound for coccidiosis illnesses and similar illnesses in animals. For treatment, this active compound has hitherto been added in a milled crystalline form to the animal feed. However, no utilisable form for administration has hitherto been found for treatment via the drinking water, for which there is a great demand in many places. In order to ensure reliable notification via the drinking water, an active compound of this type should be present in homogeneous distribution in water for about 24 hours. The active compound is practically insoluble in water. Introduced as a suspension, at the concentration for administration, it sediments out in this period.

The concentration, in water, for administration can, depending on the severity of the illness, be between 5 and 500 ppm, but is mostly between 20 and 200 ppm.

The active compound of the formula (I) is readily soluble in a variety of organic solvents, such as, for example, acetone, ethyl lactate or N-methylpyrrolidone. However, on diluting a solution of this type, in drinking water for animals, to the concentration for administration, the active compound precipitates out immediately or after a short time. Moreover, solubilisation with solubilisers, such as, for example, polyoxyethylated castor oil or polyoxyethylene-sorbitan fatty acid esters does not lead to success. The precipitation of the active compound is certainly delayed by a few hours, but not for 24 hours.

It has now been found, surprisingly, that water-miscible solutions of the active compound of the formula (I) which contain one or more polar solvents and have an alkaline reaction can be diluted in the drinking water for the animals to the concentrations for administration and do not precipitate out over the course of 24 hours.

Accordingly, the invention relates to water-miscible solutions of 1-[3-methyl-4-(4'-trifluoromethylthiophenoxy)phenyl]-3-methyl-1,3,5-triazin-2,4,6(1H,3H,5H)-trione, which are characterised in that they contain one or more polar solvents and have an alkaline reaction.

For the preparation of the solutions according to the invention, the active compound is dissolved in a polar water-soluble solvent which either has an alkaline reaction or to which a water-soluble alkaline substance is added. The latter is more advantageously likewise dissolved in the solvent, but it can also be suspended in the solvent and only dissolve in the drinking water. In this connection, the drinking water should have a pH above 7, but preferably a pH above 8, after addition of the solution of active compound.

The solution of the concentrate of active compound should not have a pH above 11 nor have a pH below 8.

The concentration of the active compound can be in the range 0.5-50%, but is preferably in a range of 1-25%.

Suitable solvents are all water-soluble solvents in which the active compound dissolves to give an adequate concentration and which are physiologically acceptable.

These comprise, from the series of alcohols, monohydric and polyhydric (particularly mono-, di- and trihydric alkanols), such as, for example, methyl alcohol ethyl alcohol, isopropyl alcohol, benzyl alcohol, glycerol, ethlylene glycol, propylene glycol, polyethylene glycols (m.w. between 200–1500), poly(oxoethylene)-poly(oxypropylene) polymers (m.w. between 200–1500), and basic alcohols, such as, for example, mono-, di- and triethanolamine. Also ethers like the cellosolves are suitable. or methyl ethyl ketone and, from the series of esters, for example, ethyl lactate. Other solvents, such as N-methylpyrrolidone, dimethylacetamide and dimethylformamide can likewise be employed.

Organic bases are preferably employed as bases to adjust the alkaline pH, for example basic amino acids, such as L- or D,L-arginine, L- or D,L-Lysine, but also choline, methylglucosamine, glucosamine and 2-amino-2-hydroxymethyl-1,3-propanediol. Diamines are also suitable for this purpose, for example, N,N,N',N'-tetrakis(2-hydroxypropyl)ethylenediamine or polyether tetrol based on ethylenediamine (M.W. 480–420, OH Index 432–467) likewise forms clear solutions in the indicated pH range. Inorganic bases can also be employed, for example ammonia or sodium carbonate, where appropriate with the addition of water.

If substances and agents which are suitable for prophylaxis and/or medication are administered to the animals at the same time as agents for coccidia, they can additionally be incorporated in the formulation in order to function as the basic component in the formulation, for example aminoglycoside antibiotics, such as streptomycin, gentamicin, sisomicin, eomicin, or macrolide antibiotics, such as tylosin or kitasamycin, or sodium salts of sulphonamides.

Substances which are otherwise used as emulsifiers or solubilisers and which are colloidally soluble in water can be employed in this case like polar solvents as long as a basic auxiliary is also added to them.

As has already been mentioned in the introduction, that it is not possible by solubilisation without the addition of substances having alkaline effects to keep the active compound in solution at the final concentration for a prolonged period. However, such emulsifiers can be added to the abovementioned, claimed solutions in order, for example, to facilitate the distribution in water or to wet suspended auxiliaries. Polyoxyethylated substances are particularly suitable for this purpose, such as, for example, polyoxyethylated castor oil, polyethylene glycolsorbitan monooleate, polyethylene glycol-nonylphenyl, polyethylene glycol stearate or polyethylene glycol ethers. Basic derivatives, such as polyethylene glycol-alkylamines are particularly advantageous for this purpose.

Solutions or suspensions of the type described above can also contain 0.1 to 20% by weight, preferably 0.1–10% by weight, of other formulation auxiliaries, such as antioxidants, other surfactants, suspension stabilisers and thickening agents, such as, for example, methylcellulose, colloidal silica and others. The addition of a colorant, flavouring and builders to the animal feed is also possible. Moreover, acids which form a buffer system together with the initially introduced base or which reduce the pH of the solution should be mentioned here.

The following examples are intended to outline the nature of the invention without thereby restricting it.

To prepare the solutions according to the invention, the substances are weighed into a container having a stirrer and then stirred, while heating, until a clear solution has been produced. In the examples listed, the active compound is stable at 50° C. for one month. If the solutions from the examples are diluted 1:1,000 with water, the pH of the water is in the range greater than 8 described above.

EXAMPLE 1

2.5 g of active compound are dissolved to 100 ml of triethanolamine by heating.

The clear solution has a pH of 10.2.

EXAMPLE 2

2.5 g of active compound and
12.5 g of lactic acid are dissolved to 100 ml in triethanolamine with heating and stirring.

The pH of the solution is 8.3.

EXAMPLE 3

10.0 g of active compound are dissolved to 100 ml of monoethanolamine.

The clear solution has a pH of 11.

EXAMPLE 4

| | |
|---|---|
| Active compound | 5.0 g |
| Propylene glycol | 50.0 g |
| Sodium carbonate | 5.0 g |
| Water ad | 100 ml |
| pH of the solution 9.9. | |

EXAMPLE 5

5.0 g of active compound
25.0 g of D,L-lysine base
ad 100 ml with polyethylene glycol 400
pH of the solution 9.8.

EXAMPLE 6

25.0 g of active compound
10.0 g of monoethanolamine
ad 100 ml with N-methylpyrrolidone pH of the solution 10.8.

What is claimed is:

1. A water-miscible concentrated solution consisting essentially of 1 to 25% by weight of 1-[3-methyl-4-(4'-trifluoromethyl-thiophenoxy)phenyl]-3-methyl-1,3,5-triazin-2,4,6(1H, 3H, 5H)-trione as the active compound, a polar organic solvent selected from the group consisting of propylene glycol and polyethylene glycol, and at least one base selected from the group consisting of triethanolamine and arginine, the concentrate upon dilution with water forming a stable solution of pH 8 to 11.

2. A water-miscible solution according to claim 1, wherein triethanolamine is employed as the base.

3. A water-miscible solution according to claim 1, wherein arginine is employed as the base.

4. A water-miscible solution according to claim 1, wherein the solvent is propylene glycol.

5. A water-miscible solution according to claim 1, wherein the solvent is polyethylene glycol.

* * * * *